US012207885B2

(12) United States Patent
McDowall et al.

(10) Patent No.: US 12,207,885 B2
(45) Date of Patent: Jan. 28, 2025

(54) TUBULAR BODY STRUCTURE IMAGING AND LOCATING SYSTEM

(71) Applicant: INTUITIVE SURGICAL OPERATIONS, INC., Sunnyvale, CA (US)

(72) Inventors: Ian E. McDowall, Woodside, CA (US); Marc Levesque, Sunnyvale, CA (US); Theodore W. Rogers, Alameda, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 449 days.

(21) Appl. No.: 16/140,709

(22) Filed: Sep. 25, 2018

(65) Prior Publication Data

US 2019/0090960 A1    Mar. 28, 2019

Related U.S. Application Data

(60) Provisional application No. 62/562,726, filed on Sep. 25, 2017.

(51) Int. Cl.
*A61B 34/20*    (2016.01)
*A61B 1/00*    (2006.01)
(Continued)

(52) U.S. Cl.
CPC .......... *A61B 34/20* (2016.02); *A61B 1/00006* (2013.01); *A61B 1/000094* (2022.02);
(Continued)

(58) Field of Classification Search
CPC ...... A61B 5/6847; A61B 5/6851–6852; A61B 2090/397; A61B 2090/3975; A61B 34/20;
(Continued)

(56) References Cited

U.S. PATENT DOCUMENTS 5,042,486 A * 8/1991 Pfeiler ................. A61B 8/0833
600/424
5,211,165 A * 5/1993 Dumoulin ............... A61B 5/06
128/899

(Continued)

FOREIGN PATENT DOCUMENTS

EP    0214712 A1    3/1987
EP    3195786 A1 *  7/2017 ............... A61B 5/72

(Continued)

OTHER PUBLICATIONS

"InfraVision Imaging System—EKIT and UKIT," Stryker, Endoscopy, 2005, 4 pages.

(Continued)

*Primary Examiner* — Serkan Akar
*Assistant Examiner* — Aminah Asghar
(74) *Attorney, Agent, or Firm* — Haynes & Boone, LLP.

(57) ABSTRACT

A system for identifying a location of a lumen of a tubular body structure in a patient's body includes a flexible, longitudinally extending probe configured to be inserted through the lumen in the tubular body structure in the patient. A detection system may include an antenna arranged to receive signals from a longitudinally extending detectable portion of the probe. A processing system may process the received signals and identify a longitudinally extending position of the longitudinally extending detectable portion of the probe in a three dimensional reference frame.

24 Claims, 7 Drawing Sheets

(51) Int. Cl.
*A61B 5/00* (2006.01)
*A61B 5/05* (2021.01)
*A61B 5/0507* (2021.01)
*A61B 5/06* (2006.01)
*A61B 5/20* (2006.01)
*A61B 34/30* (2016.01)
*A61B 34/37* (2016.01)
*A61B 90/00* (2016.01)

(52) U.S. Cl.
CPC ........ *A61B 1/00149* (2013.01); *A61B 1/0016* (2013.01); *A61B 1/00194* (2022.02); *A61B 5/05* (2013.01); *A61B 5/0507* (2013.01); *A61B 5/061* (2013.01); *A61B 5/20* (2013.01); *A61B 5/6852* (2013.01); *A61B 34/37* (2016.02); *A61B 90/37* (2016.02); *A61B 90/39* (2016.02); *A61B 1/00193* (2013.01); *A61B 5/6847* (2013.01); *A61B 2034/2046* (2016.02); *A61B 2034/2051* (2016.02); *A61B 2034/2059* (2016.02); *A61B 2034/2063* (2016.02); *A61B 2034/301* (2016.02)

(58) Field of Classification Search
CPC .... A61B 2034/2046; A61B 2034/2051; A61B 5/05; A61B 5/0507; A61B 5/064; A61B 5/06; A61B 1/00149; A61B 5/061; A61B 1/0016; A61B 34/37; A61B 5/20; A61B 1/00006; A61B 90/37; A61B 90/39; A61B 2034/2059; A61B 1/00193; A61B 2034/301; A61B 2034/2063; A61B 1/00009

See application file for complete search history.

(56) References Cited

U.S. PATENT DOCUMENTS

| | | | |
|---|---|---|---|
| 5,391,199 A | 2/1995 | Ben-Haim | |
| 5,558,091 A * | 9/1996 | Acker | A61B 5/062 600/424 |
| 6,332,089 B1 * | 12/2001 | Acker | A61B 5/0422 128/899 |
| 7,966,057 B2 * | 6/2011 | Macaulay | A61B 5/6886 600/424 |
| 8,882,657 B2 * | 11/2014 | Ohline | A61B 90/98 600/117 |
| 8,932,223 B2 | 1/2015 | Emelianov et al. | |
| 10,058,284 B2 | 8/2018 | Hoseit et al. | |
| 2001/0016762 A1 * | 8/2001 | Carr | A61M 5/44 607/101 |
| 2008/0174409 A1 * | 7/2008 | Frank | A61B 90/90 340/10.4 |
| 2010/0274256 A1 * | 10/2010 | Ritchey | A61B 34/20 606/96 |
| 2013/0072815 A1 * | 3/2013 | Hashimshony | A61B 10/0266 600/564 |
| 2013/0085510 A1 * | 4/2013 | Stefanchik | A61B 34/30 901/30 |
| 2014/0100454 A1 * | 4/2014 | Kemp | A61B 8/483 600/407 |
| 2014/0276943 A1 * | 9/2014 | Bowling | A61B 34/32 901/47 |
| 2015/0051496 A1 * | 2/2015 | Ouchi | A61B 5/0062 600/473 |
| 2016/0220314 A1 * | 8/2016 | Huelman | A61B 34/20 |
| 2016/0228095 A1 * | 8/2016 | Dalal | A61B 8/0841 |
| 2017/0273732 A1 * | 9/2017 | Gutbrod | A61B 5/026 |
| 2018/0132956 A1 * | 5/2018 | Cameron | A61B 34/76 |
| 2018/0214095 A1 * | 8/2018 | Pizaine | A61B 6/12 |
| 2018/0271607 A1 * | 9/2018 | Kralicky | A61B 34/35 |
| 2019/0151044 A1 * | 5/2019 | Black | A61B 90/53 |

FOREIGN PATENT DOCUMENTS

| | | | | |
|---|---|---|---|---|
| WO | WO-9605768 A1 | | 2/1996 | |
| WO | WO-2012033936 A2 | | 3/2012 | |
| WO | WO-2017212725 A1 * | | 12/2017 | A61B 1/00 |

OTHER PUBLICATIONS

Vaayar, One Sensor to Rule them All, Sensor Capabilities, How It Works, Retrieved from the Internet <url: https://vayyar.com/technology/>, accessed on Oct. 30, 2018, 6 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

TUBULAR BODY STRUCTURE IMAGING AND LOCATING SYSTEM

CROSS-REFERENCE TO RELATED APPLICATIONS

This application claims the benefit of the filing date of U.S. Provisional Application 62/562,726 filed Sep. 25, 2017, which is incorporated by reference herein in its entirety.

TECHNICAL FIELD

The present disclosure is directed to systems and methods for performing a medical procedure and more particularly to systems and methods for identifying and locating longitudinally extending tubular body structures in a patient during a medical procedure.

BACKGROUND

Medical robotic systems such as teleoperational systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical teleoperational systems is strong and growing.

Examples of medical teleoperational systems include the da Vinci® Surgical System and the da Vinci® S™ Surgical System from Intuitive Surgical, Inc., of Sunnyvale, Calif. Each of these systems includes a health care provider's console, a patient-side cart, a high performance three-dimensional ("3-D") vision system, and Intuitive Surgical's proprietary EndoWrist® articulating instruments, which are modeled after the human wrist. When added to the motions of manipulators holding the surgical instruments, these articulating instruments allow at least six degrees of freedom of motion to their end effectors, which is comparable to or even greater than the natural motions of open surgery.

Some surgical procedures are performed in relatively close proximity to small but important hollow body structures, such as tubes, vessels, veins, or arteries. For example, the ureter is a tubular body structure well known to present a significant challenge during various types of abdominal surgeries because it is hard to accurately locate. Avoiding accidental perforation or section of the ureter therefore requires extra caution when performing procedures in its vicinity.

To reduce the likelihood of accidental perforation or section, it would be desirable to be able to identify the position of the hollow body structures relative to a surgical instrument during a medical procedure.

SUMMARY

In general, the present disclosure is directed to systems and methods for identifying the location of a hollow tubular body structure in a patient. Some implementations use RF technology to identify a longitudinally extending position of a catheter in a tubular body structure, such as the ureter. Certain embodiments of the invention are best summarized by the claims that follow the description.

Some example aspects are directed to a system for identifying a location of a lumen of a tubular body structure in a patient's body. The system may include a flexible, longitudinally extending probe configured to be inserted through the lumen in the tubular body structure in the patient. The probe may include a longitudinally extending detectable portion. The system may also include a detection system that may include an antenna arranged to receive signals from the longitudinally extending detectable portion of the probe, and may include a processing system configured to process the received signals and identify a longitudinally extending position of the longitudinally extending detectable portion of the probe in a three dimensional reference frame.

In some additional aspects, the present disclosure is directed to systems that may include a flexible, longitudinally extending probe configured to be inserted through the lumen in the tubular body structure of the patient. The longitudinally extending probe may have a longitudinally extending detectable portion along a longitudinal length. The system may include a surgical tool arranged to interact with the patient's body to perform a surgical task on the patient, and may include a detection system. The detection system may be configured to detect a longitudinally extending position of the longitudinally extending detectable portion and compare the detected longitudinally extending position of the longitudinally extending detectable portion to a position of the surgical tool in the body to inhibit undesired interference between the tubular body structure containing the longitudinally extending detectable portion and the surgical tool.

In some aspects, the present disclosure is directed to methods that may include inserting a flexible, longitudinally extending probe through a lumen in a tubular body structure in a patient. The longitudinally extending probe may have a longitudinally extending detectable portion. The method also may include detecting a longitudinally extending position of the longitudinally extending detectable portion of the longitudinally extending probe in a three-dimensional reference frame with an antenna arranged to receive signals from the longitudinally extending detectable portion. In some aspects, the method may include determining a distance between the longitudinally extending detectable portion and a surgical tool disposed in the patient or may include determining a position of the surgical tool in the patient in a three dimensional reference frame.

In yet other example aspects, the present disclosure is directed to a system for identifying the shape of a plastic encased braided metallic structure inserted into an anatomical structure in a body. The system may include a plastic encased braided metallic structure inserted into the body through a natural orifice, with the metallic structure including a longitudinally detectable portion. A detection system may include an array of antennae arranged to bounce signals off the longitudinally extending detectable portion, and may include a processing system configured to process received signals and identify a braided metallic structure position of the longitudinally extending detectable portion of the plastic encased braided metallic structure in a three dimensional reference frame.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

DETAILED DESCRIPTION

Figure 1A:
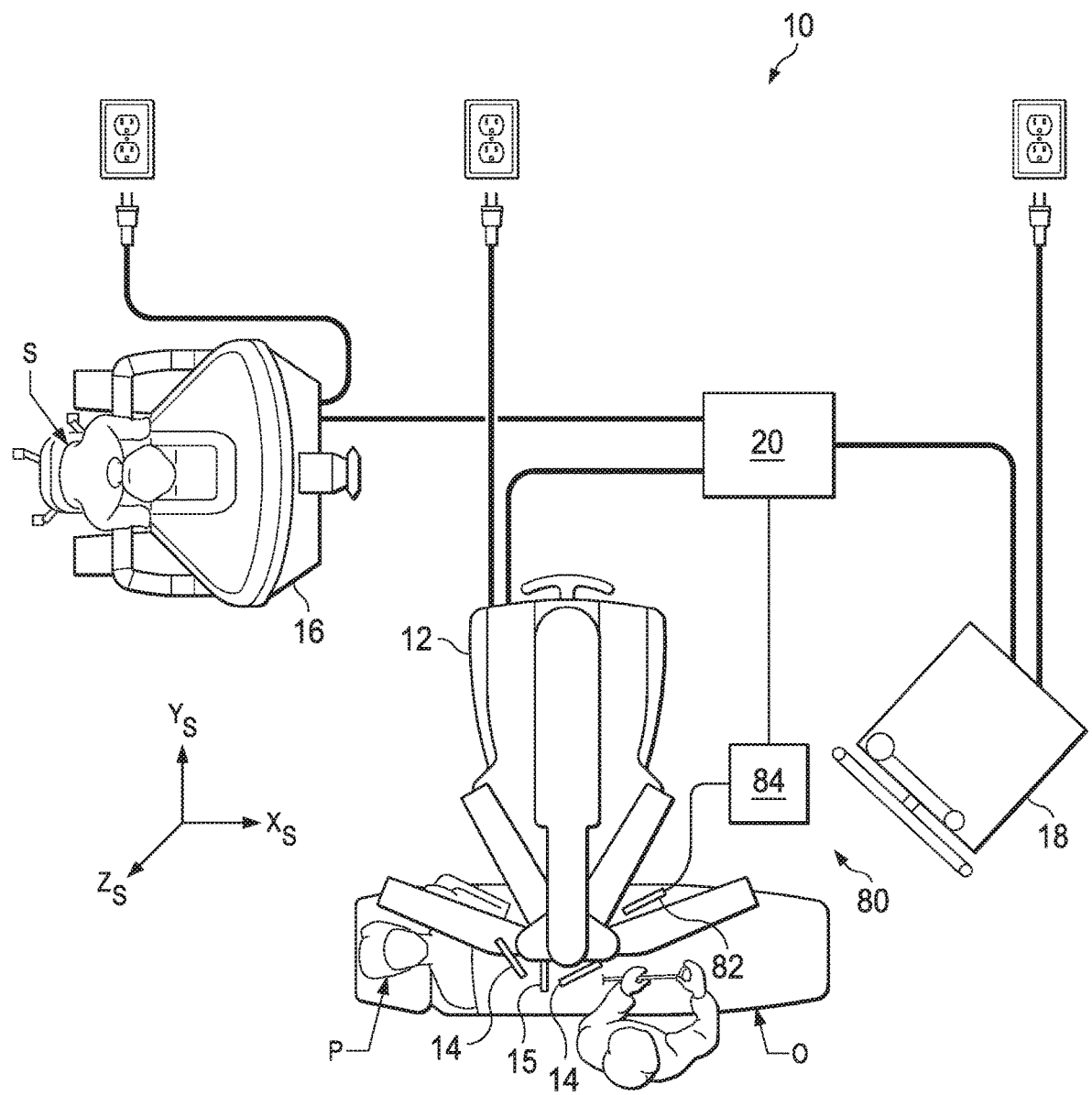
FIG. 1A is a schematic view of a teleoperated medical system in a surgical frame of reference, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1A of the drawings, a teleoperated medical system for use in, for example, medical procedures including diagnostic, therapeutic, or surgical procedures, is generally indicated by the reference numeral 10 and operates within a surgical environment having a surgical frame of reference coordinate system, XS, YS, ZS. As will be described, the teleoperated medical systems of this disclosure are under the teleoperated control of a health care provider. In alternative embodiments, a teleoperated medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperated medical system 10 generally includes a teleoperated assembly 12 mounted to or near an operating table O on which a patient P is positioned. The teleoperated assembly 12 may be referred to as a patient side cart. A medical instrument system 14 and an endoscopic imaging system 15 are operably coupled to the teleoperated assembly 12. An operator control and display system 16 allows a health care provider or other type of health care provider S to view images of or representing the surgical site and to control the operation of the medical instrument system 14 and/or the endoscopic imaging system 15. A tubular body structure position detector 80 including, for example, a longitudinally extending probe 82 and a detection system 84, may be used with the medical instrument system 14 as will be described below. Together with the patient side cart 12, the tubular body structure position detector 80 may be known as or may form a part of a patient side system. The tubular body structure position detector 80 may be a system of identifying the position of internal tubular body structures of a patient and may help reduce the likelihood of inadvertently contacting, slicing, or otherwise damaging of the tubular body structure undergoing a procedure with the teleoperated medical system 10. Note that the longitudinally extending probe or the detection system with hardware associated with the tubular body structure position detector 80 may be part of the operating room table O, placed on operating room table O either under or on top of the patient, or may be implemented as a tool deployed on teleoperated assembly 12.

The operator control and display system 16 (also called a console) may be located at a health care provider's console, which is usually located in the same room as operating table O. It should be understood, however, that the health care provider S can be located in a different room or a completely different building from the patient P. The health care provider's console 16 includes left and right eye displays for presenting the health care provider S with a coordinated stereo view of the surgical site that enables depth perception. The console 16 further includes one or more input control devices which cause the teleoperated assembly 12 to manipulate one or more instruments or the endoscopic imaging system. The input control devices can provide the same degrees of freedom as their associated instruments 14 to provide the health care provider S with telepresence, or the perception that the input control devices are integral with the instruments 14 so that the health care provider has a strong sense of directly controlling the instruments 14. To this end, position, force, and tactile feedback sensors (not shown) may be employed to transmit position, force, and tactile sensations from the instruments 14 back to the health care provider's hands through the input control devices. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperated assembly to provide the health care provider with telepresence, the perception that the control device(s) are integral with the instruments so that the health care provider has a strong sense of directly controlling instruments as if present at the surgical site. In other embodiments, the control device(s) may have more or fewer degrees of freedom than the associated medical instruments and still provide the health care provider with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperated assembly 12 supports and manipulates the medical instrument system 14 while the health care provider S views the surgical site through the console 16. An image of the surgical site can be obtained by the endoscopic imaging system 15, such as a stereoscopic endoscope, which can be manipulated by the teleoperated assembly 12 to orient the endoscope 15. An electronics cart 18 can be used to process the images of the surgical site for subsequent display to the health care provider S through the health care provider's console 16. The number of medical instrument systems 14 used at one time will generally depend on the diagnostic or surgical procedure and the space constraints within the operating room among other factors. The teleoperated assembly 12 may include a kinematic structure of one or more non-servo controlled links (e.g., one or more links that may be manually positioned and locked in place, generally referred to as a set-up structure) and a teleoperated manipulator. The teleoperated assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperated medical system 10 also includes a control system 20. The control system 20 includes at least one memory and at least one processor (not shown), and typically a plurality of processors, for effecting control between the medical instrument system 14, the endoscopic system 15, the operator control and display system 16, and monitors on the electronics cart 18. The control system 20 may also receive and process location information, generated images, or data from the tubular body structure position detector 80. The electronics cart 18 may house components of the endoscopic imaging system 15, the tubular body structure position detector 80, the control system 20 as well as monitors and processors for processing and displaying captured images.

The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperated assembly 12, another portion of the processing being performed at the operator control and display system 16, and the like. Any of a wide variety of centralized or distributed data processing architectures may be employed. Similarly, the programmed instructions may be implemented as a number of separate programs or subroutines, or they may be integrated into a number of other aspects of the teleoperated systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator control and display system 16. The servo controller(s) may also transmit signals instructing teleoperated assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperated assembly 12. In some embodiments, the servo controller and teleoperated assembly are provided as part of a teleoperated arm cart positioned adjacent to the patient's body.

The teleoperated medical system 10 may further include optional operation and support systems (not shown) such as illumination systems, steering control systems, irrigation systems, and/or suction systems. In alternative embodiments, the teleoperated system may include more than one teleoperated assembly and/or more than one operator control and display system. The exact number of manipulator assemblies will depend on the surgical procedure and the space constraints within the operating room, among other factors. The operator control and display systems may be collocated, or they may be positioned in separate locations.

Figure 1B:
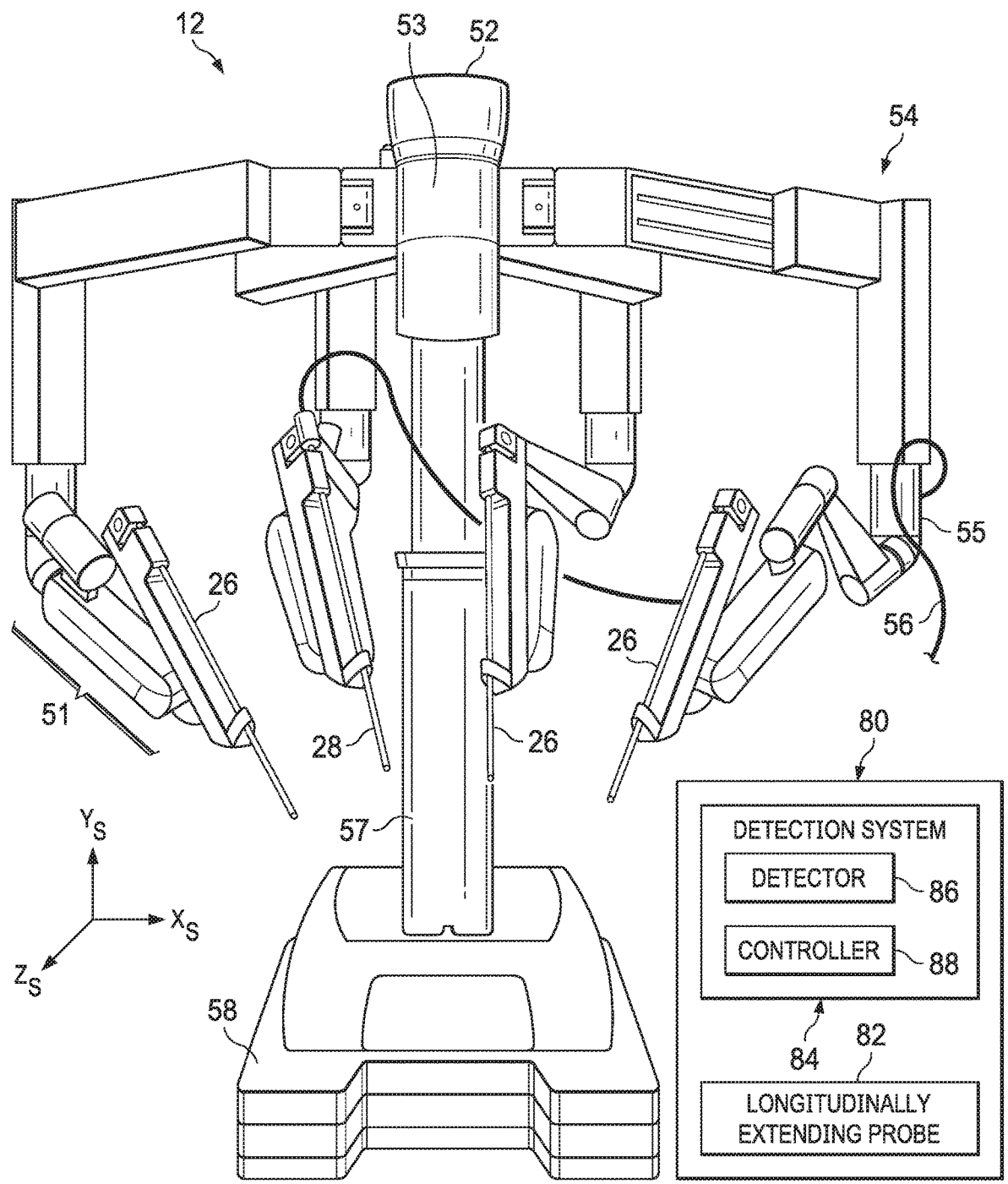
FIG. 1B is a perspective view of patient side systems, according to one example of principles described herein.

FIG. 1B is a perspective view of one embodiment of a teleoperated assembly 12 and a block diagram of the tubular body structure position detector 80. The teleoperated assembly 12 shown provides for the manipulation of three surgical tools 26 (e.g., instrument systems 14) and an imaging device 28 (e.g., endoscopic imaging system 15), such as a stereoscopic endoscope used for the capture of images of the site of the procedure. The imaging device may transmit signals over a cable 56 to the electronics cart 18. Manipulation is provided by teleoperative mechanisms having a number of joints. The imaging device 28 and the surgical tools 26 can be positioned and manipulated through incisions or natural orifices in the patient so that a kinematic remote center is maintained at the incision to minimize the size of the incision. Images of the surgical site can include images of the distal ends of the surgical tools 26 when they are positioned within the field-of-view of the imaging device 28.

The teleoperated assembly 12 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The teleoperated assembly may also include a telescoping horizontal cantilever 52 (in and out of the page in this view) for moving the orienting platform 53 in a horizontal direction.

In the present example, each of the arms 54 connects to a manipulator arm 51. The manipulator arms 51 may connect directly to surgical tools 26. The manipulator arms 51 may be teleoperable. In some examples, the arms 54 connecting to the orienting platform are not teleoperable. Rather, such arms 54 are positioned as desired before the health care provider begins operation with the teleoperative components.

The tubular body structure position detector 80 may cooperate with the teleoperated assembly 12 and the control system 20 (FIG. 1A) to identify the position of a tubular body structure. By knowing the position, there may be a reduced likelihood of inadvertently contacting, slicing, or otherwise damaging a tubular body structure of a patient undergoing a procedure with the teleoperated medical system 10. As used herein, reference to a tubular body structure is intended to include a hollow tube, vessel, vein, or artery or other body structure within the human body having a longitudinally extending lumen. As an example, a tubular body structure may refer to a ureter extending between the kidney and the bladder in a patient body. The tubular body structure position detector 80 identifies in three-dimensional reference frame a longitudinally extending portion of a tubular body structure.

The tubular body structure position detector 80 includes, for example, a longitudinally extending probe 82 and a detection system 84. In some implementations, the longitudinally extending probe 82 is a catheter insertable into a longitudinally extending tubular body structure of the patient. The catheter may be a hollow flexible tube (for example constructed with a braided metallic mesh embedded in the wall of a plastic or other compliant material creating a tubular structure) or a solid flexible wire that may be inserted into a tubular body structure. In the embodiment shown, the longitudinally extending probe 82 includes a braided metallic mesh embedded in a wall of a plastic, referenced by the numeral 83. In some implementations, the extending probe 82 includes a rounded end to reduce the likelihood of damage or trauma to an inner wall of a tubular body structure as the extending probe 82 is advanced along the lumen of the tubular body structure. The longitudinally extending probe includes a longitudinally extending detectable portion along its longitudinal length. In some implementations, the longitudinally extending detectable portion extends along the entire length of the longitudinally extending probe, while in other implementations the longitudinally extending detectable portion extends only along a partial length of the longitudinally extending probe. The longitudinally extending detectable portion may be made of a material detectable via RF or microwaves such that its position may be identifiable in the three-dimensional reference frame. This may be for example a metal wire, cable, tube, or conduit or other RF or microwave detectable material.

Depending on the particular implementation, the longitudinally extending detectable portion may be disposed at or adjacent a distal tip of the longitudinally extending probe 82 or may be spaced proximal from the distal tip. In some implementations, the longitudinally extending detectable portion has a length in a range of about 1 inch to 120 inches, although larger and smaller lengths are contemplated. In some implementations, the longitudinally extending detectable portion has a length between about 3 inches to 120 inches. Some implementations include a camera at a distal end of the longitudinally extending probe 82. In such instances, electrical conduits extending from the camera to a proximal end of the extending probe may be the longitudinally extending detectable portion. In some implementations, the longitudinally extending detectable portion is formed of a series of non-longitudinally extending identifiers, arranged in a row along the longitudinally extending probe 82. For example, one implementation may include twenty identifiers equally spaced along the longitudinally extending probe 82, with the spacing close enough together to be able to show curves or turns or the longitudinally extending shape of the longitudinally extending detectable portion. When the longitudinally extending probe 82 is within a longitudinally extending tubular body structure, such as a ureter, the tubular body structure's location may be identified by identifying the location of the longitudinally extending probe 82. Accordingly, the location of the longitudinally extending probe 82 represents the location of the tubular body structure in which it lies.

The detection system 84 may include a detector 86 and a controller 88. The detector 86 may be configured to receive signals from the longitudinally tracking probe 82 that may be indicative of its longitudinally extending position in the three-dimensional reference frame. In some implementations, detector 86 may be configured to receive radio-frequency (RF) signals or microwave signals from the longitudinally extending probe 82. Depending on the implementation, the detector 86 may be or may comprise a series of antennas forming an antenna array that may receive RF signals or microwave signals from the longitudinally extending probe 82. In some implementations, the detector 86 may have only signal receiving capability, while in other implementations, the detector 86 may have transmitting and receiving capabilities. For example, the detector 86 may include RF transmitters or microwave transmitters that transmit RF signals or microwave signals from a single transmitter, and may receive reflected signals along an array of antennas. In other examples, detector 86 may include a series of RF transceivers or microwave transceivers each respectively transmitting RF signals or microwave signals toward the longitudinally extending probe 82, and receiving reflected signals back at a series or an array of antennas. Some implementations include a pad upon which an array of antennas may be disposed. The pad may be disposed on the operating table O (FIG. 1) and the patient may lie upon the pad during a surgical procedure. In some implementations, the longitudinally extending probe is not employed and only the pad detector 86 with an array of RF transceivers are used.

The controller 88 may be configured to receive signals from the detector 86 and process the signals to determine a location of the longitudinally extending probe 82 in the three-dimensional reference frame. Since the detection system 84 is configured to identify a longitudinally extending length of the longitudinally extending probe 82, the array of antennas used by the detector 86 may include at least 3 or more antennas. Accordingly, the controller 88 may include a processor and a memory with executable instructions to determine and identify in the three-dimensional reference frame the shape and location of the longitudinally extending probe 82 relative to the detector 86. Some implementations determine the location of a longitudinally extending length by identifying at a plurality of points along the longitudinally extending probe 82, the location in a surgical frame of reference coordinating system XS, YS, and ZS. This may be the same coordinate system within which the teleoperated assembly operates, or may be a different surgical reference frame. The plurality of points along the length may be assembled by the control system to represent an axis or line, a curve, or a curved path or axis along which the longitudinally extending probe extends. Although the controller 88 is shown as a part of the tubular body structure position detector 80, in some implementations, the controller 88 is disposed in or forms a part of the control system 20 (FIG. 1). In such implementations, the detector 86 may communicate directly with the control system 20. As indicated above, the longitudinally extending probe 82 represents the lumen in which it is disposed. Accordingly, by identifying in the three-dimensional reference frame the position of the longitudinally extending probe 82, the controller 88 also identifies the position of the tubular body structure, such as the ureter, in which it is disposed.

Endoscopic imaging systems (e.g., systems 15 and/or 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image based endoscopes have a "chip on the tip" camera design in which a distal digital sensor such as a one or more charge-coupled device (CCD) or a complementary metal oxide semiconductor (CMOS) device acquire image data. Endoscopic imaging systems may provide two- or three-dimensional images of the endoscopic field of view (i.e. the imaging area) to the viewer. Two-dimensional images may provide limited depth perception. Three-dimensional stereo endoscopic images may provide the viewer with more accurate depth perception. Stereo endoscopic instruments employ stereo cameras to capture stereo images of the field of view of the patient anatomy. An endoscopic instrument may be a fully sterilizable assembly with the endoscope cable, handle and shaft all rigidly coupled and hermetically sealed.

Figure 2:
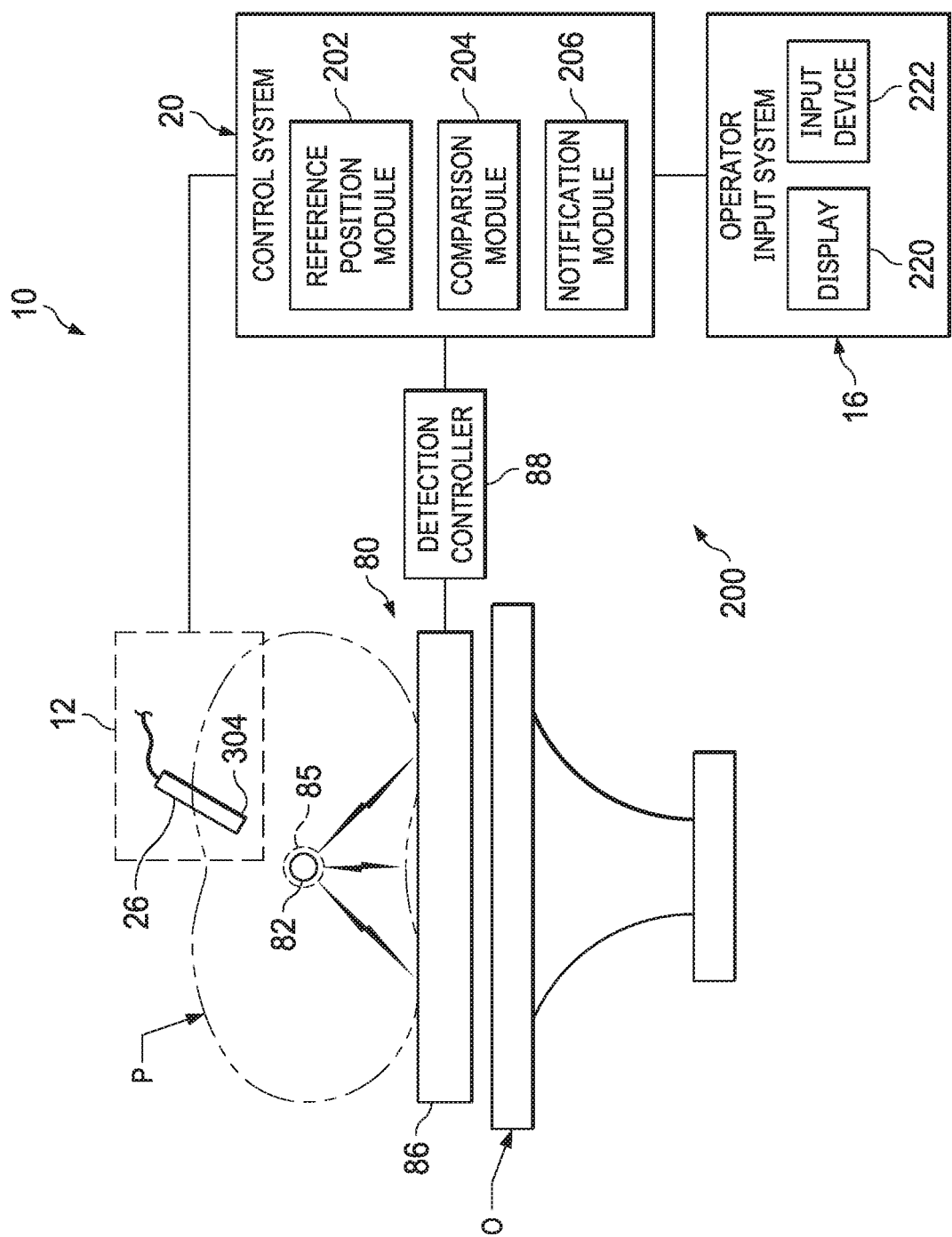
FIG. 2 is a block diagram of a system for identifying a location of a lumen of a tubular body structure in the patient's body during a medical procedure according to some embodiments.
Figure 3:
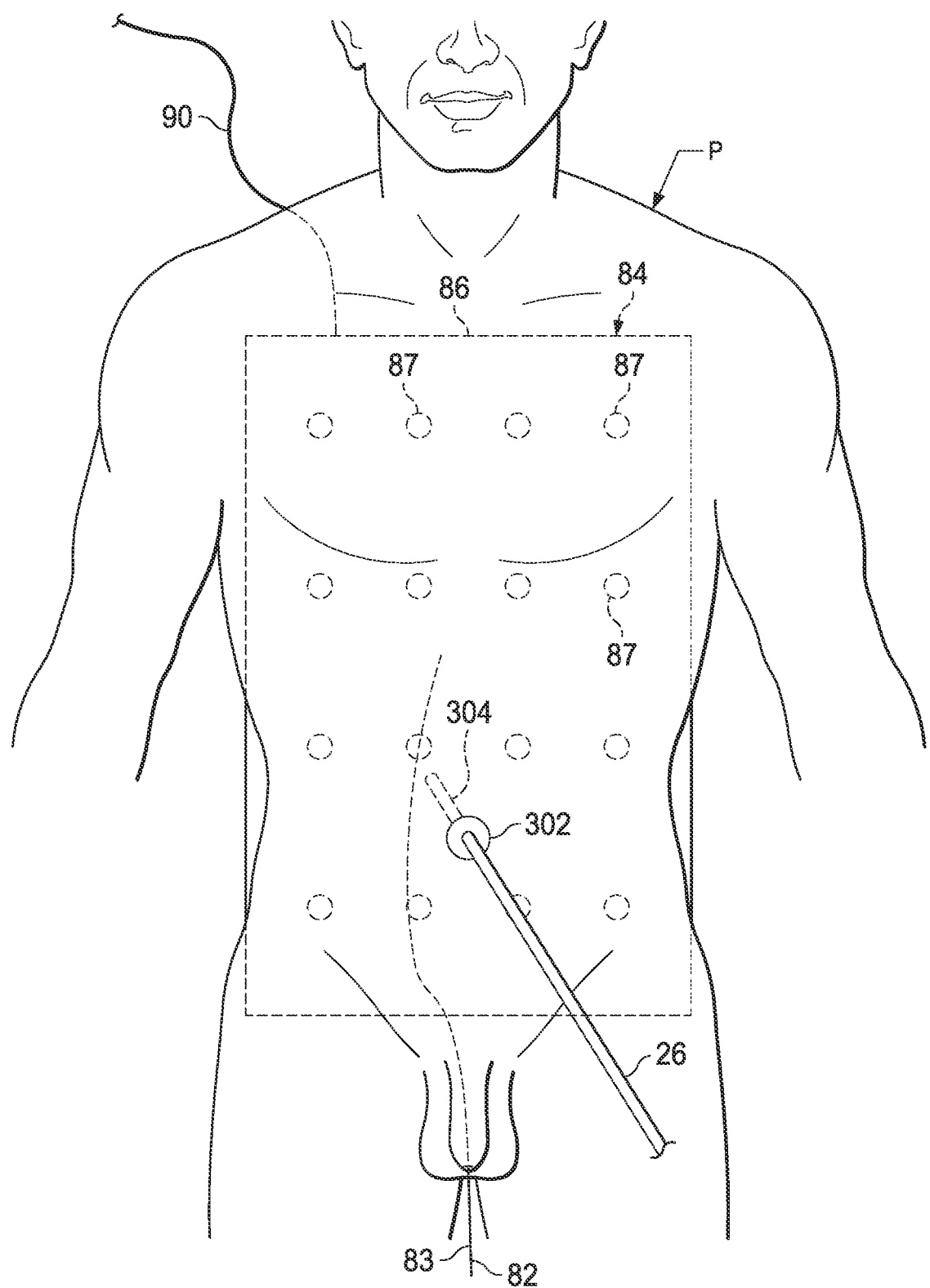
FIG. 3 is a simplified illustration of a patient body with components of a tube position detector for identifying a position of a longitudinally extending probe, such as a catheter in a tubular body structure according to some embodiments.

Additional functionality of the teleoperated medical system 10 will be described with reference to FIGS. 2 and 3. FIG. 2 is a block diagram of a system 200 and a patient body P for identifying the location of the lumen in a tubular body structure 85 of a patient's body P. FIG. 3 illustrates a patient body with example components of a tubular body structure position detector for identifying a position of a catheter 82 in a tubular body structure L according to some embodiments.

FIG. 2 shows the teleoperated medical system 10 in block diagram form arranged to detect the longitudinally extending probe 82 disposed in a body of a patient P, according to an example implementation. The teleoperated medical system 10 includes the teleoperated assembly 12 with a surgical tool 26 extending into the body of the patient P and with the longitudinally extending probe 82 disposed in a tubular body structure of the patient P. In this implementation, the tubular body structure position detector 80 is shown with the longitudinally extending probe 82 disposed in a tubular body structure 85 of the patient P and the detector 86 disposed below the patient P external to the body. As described above, in some implementations the detector 86 is an antenna array that may be disposed adjacent to the patient. Although shown adjacent to the patient, the detector 86 may be disposed at locations apart from the location of the patient, however some implementations may provide a greater level of location accuracy if the detector 86 is disposed close to the patient. Accordingly, in the implementation shown, the detector may lie below the patient P on the operating table O or is built into the surface of the OR table O.

FIG. 3 also shows an example of a body of a patient P with a part of the detection system 84 disposed below a portion of the patient. In FIG. 3, the detector 86, shown as an antenna array mat, includes an array of sixteen antennas 87 arranged in a 4×4 configuration in order to detect in a three-dimensional reference frame a longitudinal length of the longitudinally extending probe 82. The array shown is merely exemplary, and the antennas may be arranged in other configurations, and the detector 86 may include more or may include fewer antennas. Also in FIG. 3, the longitudinally extending probe 82 is disposed extending through body regions representing the urethra, the bladder, and the ureter, approaching the kidneys. In this implementation, the longitudinally extending probe 82 extends at a position above the detector 86 in a manner that permits the detector 86 to receive RF emissions either emitted by or reflected from the longitudinally extending probe 82. A cable 90 extends from the detector 86 to the detection controller 88.

FIG. 3 also shows the surgical tool 26 which may extend into the body of the patient P to perform a surgical procedure. FIG. 3 shows the location of a cannula seal 302 through which the surgical tool 26 may pass to enter the patient, and also shows the instrument distal tip 304.

Referring to both FIGS. 2 and 3, and as described herein, the detection controller 88 of the position detector 80 is arranged to calculate or determine in a three-dimensional reference frame the position of a longitudinal length of the longitudinally extending probe 82. The longitudinal length may be a distal region sufficient to identify a tubular body structure of interest, such as about 10-12 inches for a ureter for example. The longitudinal length may be longer or shorter depending upon the tubular body structure of interest. In some implementations, the longitudinal length may be much greater than a length of the tubular body structure of interest. As indicated herein, some implementations have a longitudinal length that extends the complete length of the longitudinally extending probe.

In FIG. 2, signals emitted by or reflected from the longitudinally extending probe 82 are detected at the detector 86. The detection controller 88 receives information from the detector 86 and processes the information according to stored computer executable instructions to determine in a three-dimensional reference frame the position and shape of the longitudinally extending probe 82 relative to the detector 86. The controller 88 may then communicate information relating to the position and shape of the longitudinally extending probe 82 to the control system 20.

The control system 20 is in communication with the teleoperated assembly 12 and includes a reference position module 202, a comparison module 204, and a notification module 206. The reference position module 202 may be a sequence of executable code with instructions to calculate the position of the surgical tool 26 in a three-dimensional reference frame. In some implementations, the reference position module 202 continuously calculates the position of the surgical tool 26 in a three-dimensional reference frame on a real-time basis at all times during a surgical procedure. In some implementations, the reference position module 202 calculates the position of the surgical tool 26 in the three-dimensional reference frame only during selected portions of the surgical procedure. In some implementations, the reference position module 202 may continuously calculate the position of a working end or distal tip 304 of the surgical tool 26 during a medical procedure. Depending upon the implementation, the reference position module 202 may be configured to identify or calculate the position of the working end or distal tip 304 based upon a series of calculations taking into account the known length and angle of the arms 54, the rotating joints 55, the orienting platform 53, the telescoping horizontal cantilever 52, the manipulator arm 51, and the particular surgical tool 26 being carried by the manipulator arm 51 (all of which are shown in FIGS. 1A and 1B) and the relative position and pose of the surgical table. In some implementations, the reference position module 202 may calculate not only the position of the working end or distal tip 304 of the surgical tool 26, but may also calculate the longitudinally extending position of portions of the surgical tool 26. For example, the reference position module 202 may calculate the location of the support structure of the surgical tool 26 leading to the distal tip 304.

The comparison module 204 includes computer implementable instructions for determining the distance between the surgical tool 26 and the longitudinally tracked portion of the longitudinally extending probe 82. To do this, the comparison module 204 is arranged to receive information from the reference position module 202 and the detection controller 88 relating respectively to the three-dimensional position of the surgical tool 26 and the longitudinally extending probe 82. In order to provide a comparison, the comparison module 204 may align or merge reference points from the control system 20 and the detection controller 88 so that the surgical tool 26 and the longitudinally extending probe 82 are both tracked within a common three-dimensional reference frame. For example, the reference position module 202 may calculate the three-dimensional location of the surgical tool 26 relative to the orienting platform 53. Likewise, the controller 88 may calculate the three-dimensional location of the longitudinally extending probe 82 relative to the detector 86. In some implementations, the comparison module 204 determines the location of the detector 86 relative to the orienting platform 53 so that the comparison module 204 may then determine the location of the longitudinally extending probe 82 relative to the orienting platform 53. While the orienting platform 53 was used as an example as a common reference point, other common reference points may be used. In some implementations, the common reference point is a point on the operating table O convenient to both the tubular body structure position detector 80 and the teleoperated assembly 12.

After aligning the reference frames of the detector 86 and the teleoperated assembly 12, the comparison module 204 may calculate the distance between any portion of the tracked longitudinally extending probe 82 and the surgical tool 26. In some implementations, this tracked distance or a representation of the distance is continuously displayed and updated in real time on the operator control and display system 16. The operator control and display system 16 may include a display 220 and one or more input devices exemplified by input device 222. The display 220 may be any of the display elements described herein including, without limitation, the left and right eye displays for presenting the health care provider S with a coordinated stereo view of the surgical site that enables depth perception. The display may also include monitors, touchscreens, video screens, or other visual display. The input device may be, for example and without limitation, a keyboard, mouse, touchscreen display, or any of the input elements described herein, including hand grips, joysticks, trackballs, data gloves, trigger-guns, hand-operated controllers, voice recognition devices, touch screens, body motion or presence sensors, and the like. In some implementations, a health care provider S (FIG. 1) may have distance information viewable at any point during the surgical procedure. In other implementations, the determined distance may be displayed only when particular settings are set, or in other implementations displayed only when preset conditions on the control system 20 determine that the information is relevant to the procedure.

Figure 4:
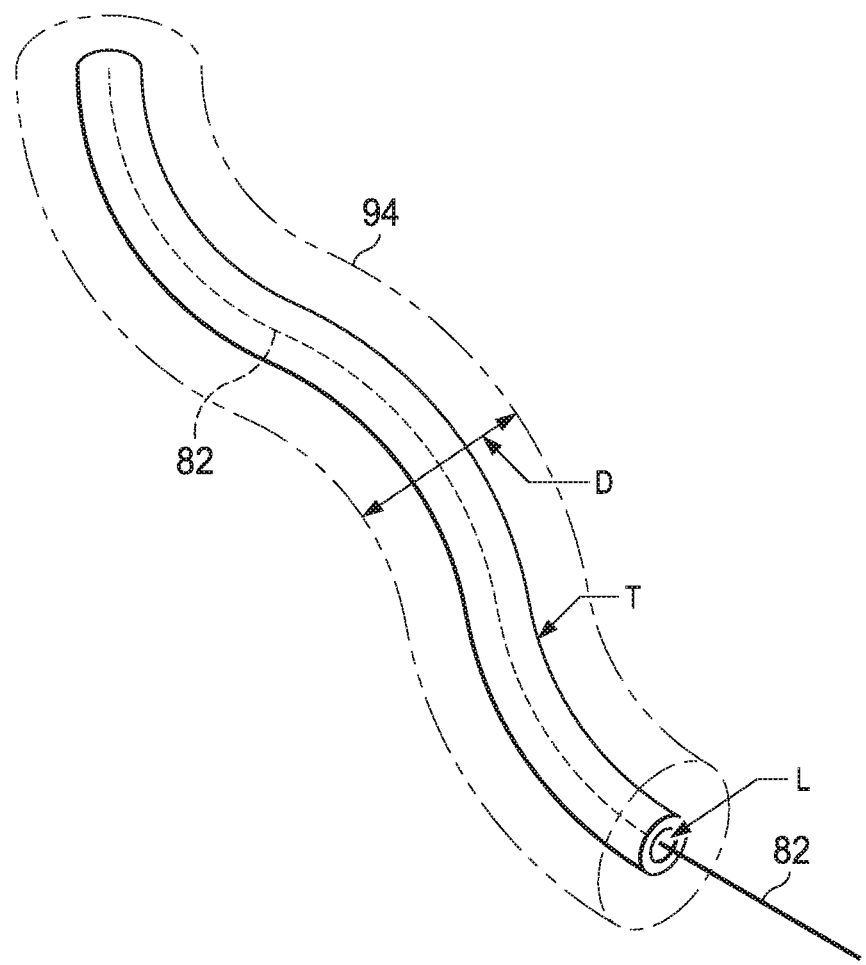
FIG. 4 is a simplified illustration of a tubular body structure having a longitudinally extending probe disposed therein, and a pre-established distance threshold encompassing the tubular body structure.

In the implementation described herein, the control system 20 includes a notification module 206 arranged to notify the health care provider S or other healthcare provider when the distance between the longitudinally extending probe 82 and the surgical tool 26 falls below a preset distance threshold. FIG. 4 shows an example preset distance threshold that may be established about a longitudinally extending portion of the longitudinally extending probe 82. In FIG. 4, a longitudinally extending lumen L of a tubular body structure T includes the longitudinally extending probe 82 disposed therein. Although the lumen L may be any portion of the patient's body, in this implementation the lumen L may be considered the ureter. The control system 20 may calculate a reference boundary 94 about the known position of the extending probe 82. The reference boundary may follow the shaper curves of the extending probe 82. Since it is desirable to avoid undesired interference such as inadvertent slicing or sectioning of the tubular body structure T, the reference boundary 94 may be established to have a diameter large enough to completely encompass the tubular body structure T. As a safety factor, the reference boundary 94 may be established to have a diameter that provides an additional safety zone about the outside of the tubular body structure T. For example, a typical ureter may have a diameter in the range of about 3 to 4 mm. After adding the safety factor, the reference boundary 94 may be established to have a diameter in the range of about 10 to 12 mm. The outer diameter of the reference boundary 94 may define the distance threshold. For tubular body structures having relatively small diameters like the ureter, the reference boundary 94 may be about 2.5 times larger than a typical diameter. Other ratios are also contemplated. In some implementations, the size of the reference boundary 94 defining the distance threshold may be established and prestored in the control system 20 or the controller 88. In some implementations, the prestored distance threshold may be adjusted manually by the health care provider S or another healthcare provider. Such adjustments may occur when developing the surgical plan or otherwise preparing for the surgical procedure.

Returning to FIG. 2, in the implementation described herein, when the surgical tool 26 breaks or intersects with the reference boundary 94, the notification module 206 issues a notification to the health care provider S or other healthcare provider alerting him or her that the surgical tool 26 is closer to the longitudinally extending probe 82 or the tubular body structure than the preset distance threshold. This notification may be made in any form that would alert the operator. In some instances, the notification is a visual notification that appears on the display 220 of the operator control and display system 16. For example, the notification module 206 may generate and send an alert that will flash in a corner of the display 220. The alert may be seen in other ways, such as, without limitation, flashing of the line representing the ureter, changing colors of the visual images, displaying textual message alerts, or other visual notifications. In other examples, the notification module 206 may activate an audible alarm that warns the health care provider of the surgical tool 26 being too close to the longitudinally extending probe 82, and therefore the tubular body structure. Other notifications may include a tactile alert. Some visual alerts are not on the display 220, but appear elsewhere about the surgical room or elsewhere, such as on other remote monitors. After receiving the notification, the health care provider S may use the input device 222 of the control and display system 16 to displace the surgical tool away from the longitudinally extending probe 82 to a safer distance, thereby protecting the tubular body structure. In some implementations, the health care provider S may need to complete a procedure within the reference boundary 94 before the surgical tool 26 may be moved away from the tubular body structure. In such instances, the health care provider S may continue the surgical procedure with knowledge of the proximity of the tubular body structure, and may take additional care to try to protect the tubular body structure while completing the surgical procedure. In some instances, the control system 20 may automatically prevent the surgical tool 26 from entering or passing further into the distance threshold. In such instances, the control system 20 may override any operator input at the input device 222 that would move the surgical tool 26 closer to the longitudinal tubular body structure. Although shown as separate components in FIG. 2, the detection controller 88 may be a module of the control system 20. Other forms of ureter protection are also contemplated including using a notification that is tactile 'force fields' which present a tactile sensation as the boundary 94 is crossed but the surgeon is still permitted to move into the volume 94.

Figure 5:
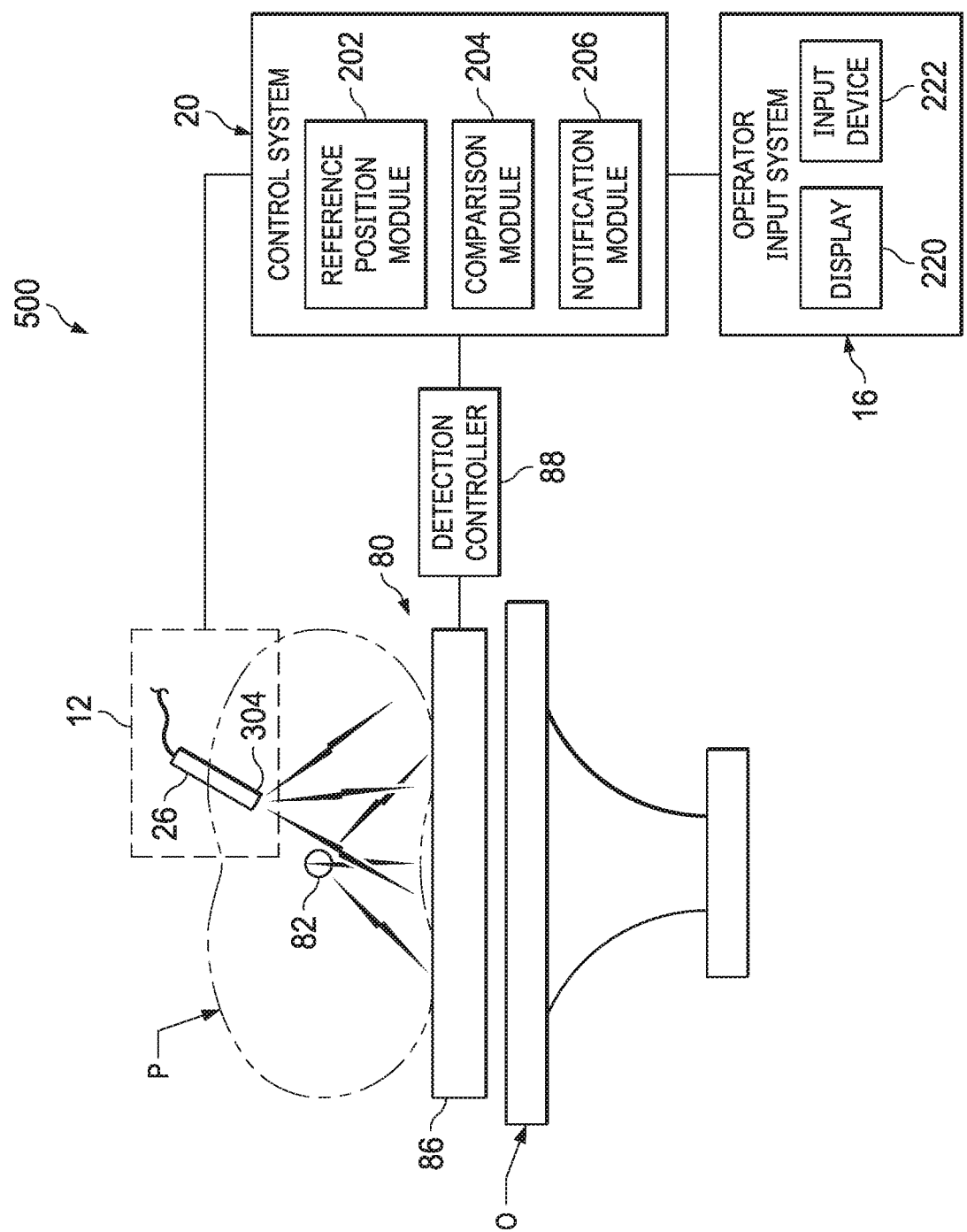
FIG. 5 is a block diagram of a modified system for identifying a location of a lumen of a tubular body structure in the patient's body during a medical procedure according to some embodiments.

FIG. 5 shows an alternative teleoperated medical system referenced by the numeral 500. Much of the teleoperated medical system 500 is the same as the teleoperated medical system 10 described herein, and the similar elements will not be redescribed in detail. The teleoperated medical system 500 differs from the teleoperated medical system 10 in that the tubular body structure position detector 80 determines the location of both the longitudinally extending probe 82 and the surgical tool 26. In so doing, the positions of the longitudinally extending probe 82 and the surgical tool 26 are detected within the same three-dimensional frame of reference. This may eliminate the need to align or merge different frames of reference as may be done using the teleoperated medical system 10. As can be seen, in this instance, the surgical tool 26 may be configured to emit RF or microwave signals that may be detected by the detector 86 or may be configured to reflect RF or microwave signals that may be generated and transmitted toward the surgical instrument.

Figure 6:
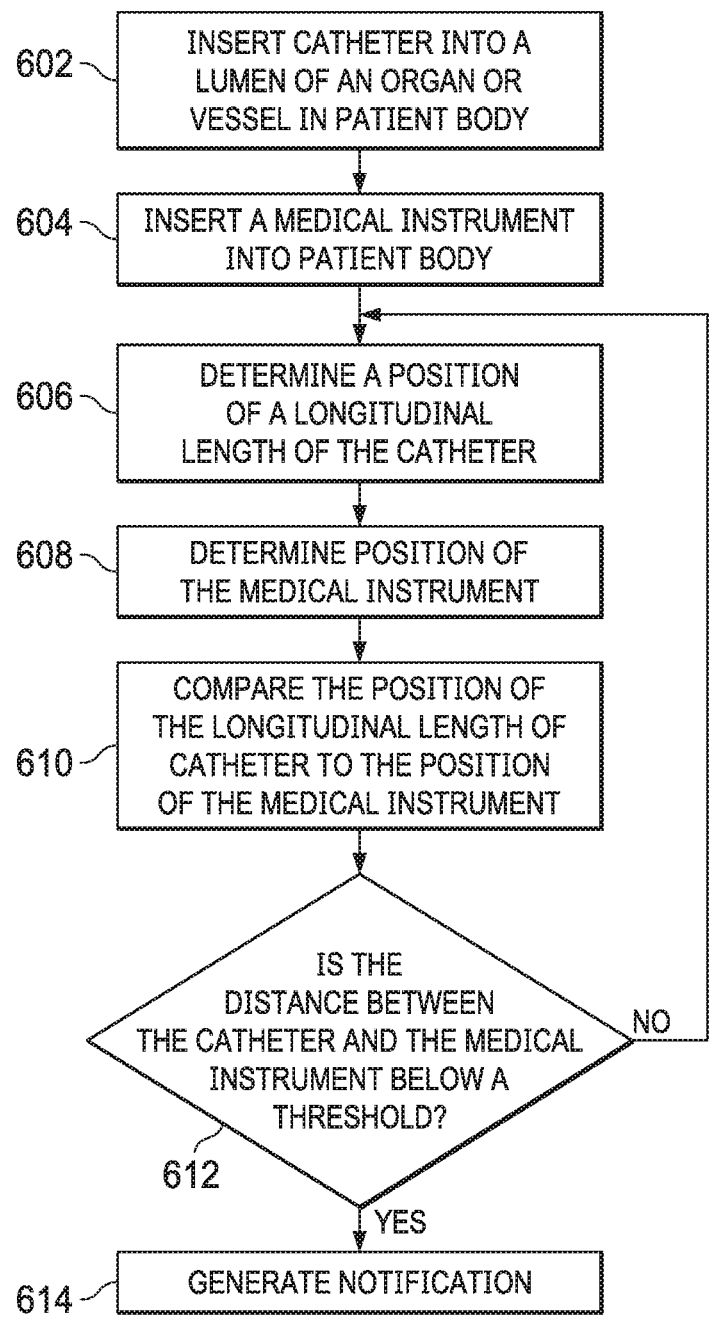
FIG. 6 is a simplified flow diagram of a method of identifying a position of a probe in a tubular body structure during a medical procedure according to some embodiments.

FIG. 6 is a simplified diagram of a method 600 for identifying the location of the tubular body structure in a patient's body. According to some embodiments, the method may be performed using, for example, the teleoperated medical system 10 or 200 or 500 as described herein. The method may be performed upon a patient lying on an operating table. In some implementations, a detector, such as the antenna array described herein which may be in the form of a mat, may be disposed on the table beneath the patient. In other implementations, the detector may be disposed elsewhere such as above the patient, to the side of the patient or anywhere about the patient. In preferred implementations, the detector is disposed external of the patient but within proximity to the patient so as to provide sufficient accuracy in detecting the position of a longitudinally extending probe, such as a catheter.

At 602, the longitudinally extending probe is inserted into a lumen of a tubular body structure in the patient body. In implementations where the tubular body structure to be tracked is a ureter, the longitudinally extending probe may be a catheter introduced through the urethra, the bladder, and the lumen of the ureter. Insertion of the longitudinally extending probe may be performed using techniques known in the art.

At 604, a medical instrument, such as surgical tool 26, is inserted into a patient body. The medical instrument provides one or more functionalities applicable to the medical procedure. According to some examples, the medical instrument may be inserted into the patient body through a cannula that extends into the body. In some implementations, the medical instrument is introduced into the body using any of the arms or components of the manipulatable teleoperated assembly 12. This may be under the direction and the control of the health care provider S as he or she directs the teleoperated assembly 12 using the operator control and display system 16 in FIG. 1. With both the longitudinally extending probe and the medical instrument disposed within the body, a health care provider S may perform a surgical procedure to treat a medical condition. The surgical procedure may be any procedure that may be performed using a teleoperated medical system.

At 606, the teleoperated medical system 10 may determine a position of a longitudinal length of the longitudinally extending probe in a three-dimensional reference frame. This may be done using a detector having one or more antennas capable of receiving RF or microwave signals indicative of location information relative to the detector. As described herein, some implementations employ an antenna array configured to receive signals either transmitted by or reflected by the longitudinally extending probe. The signals may be processed by an independent controller or by the control system of the teleoperated medical system computer according to an executable instruction module to determine the location of a continuous line or points along a line corresponding to the longitudinally extending probe in a three-dimensional reference frame. Since the longitudinally extending probe is disposed within a lumen of a tubular body structure, the location of the longitudinally extending probe is indicative and represents the location of the lumen of the tubular body structure. In some implementations, the position of the longitudinally extending probe is determined in real time, such that any changes in location that may occur by displacement of the patient or the body may be taken into account.

At 608, the position of the medical instrument, such as the surgical tool 26, is determined. Some implementations directly calculate the position of the medical instrument in a three-dimensional reference frame. For example, since the dimensions and shapes of the arms, joints, and other mechanical features of the teleoperated assembly 12 are known, the position of the instrument tip 304 or any portion of the instrument carried by the teleoperated assembly 12 may be calculated relative to a reference point. In some implementations, this calculation occurs at the control system for the teleoperated medical system 10. In preferred implementations, the position of the instrument tip or any portion of the instrument occurs in real time so that the control system is constantly aware of the precise location of the medical instrument. Instead of directly calculating the position of the medical instrument, other implementations detect the position of the medical instrument. For example, the medical instrument may be configured to emit or reflect RF or microwave signals receivable at the detector and based on the signals, the detection system may determine the location of the instrument tip or a larger portion of the surgical instrument in a three-dimensional reference frame. In such systems, the positions of both the medical instrument and the longitudinally extending probe may be determined in the same reference frame. Some implementations show both the surgical tool and the longitudinal length of the longitudinally extending probe in the display of the teleoperational system. In some cases, the control system may be arranged to overly an image of the longitudinally extending probe or the tubular body structure through which extends on the viewable image seen by a health care provider during the surgical procedure, for example on console 16.

At 610, the control system compares the position of the longitudinal length of the longitudinally extending probe to the position of the medical instrument. Depending on the implementation, this may include merging or aligning the three-dimensional reference frame of the longitudinally extending probe to the three-dimensional frame of the medical instrument. This may be done using principles known in the art, including overlaying the known reference frames. With the two components having aligned or the same reference frame, the comparison may determine the distance between the longitudinal length of the longitudinally extending probe and the medical instrument. The distance may be displayed to the health care provider or others on a display of the operator control and display system 116.

At 612, the control system 20 may determine whether the distance between the longitudinally extending probe in the medical instrument is below a preset distance threshold. As described herein, some implementations include a preset distance threshold that may be used to indicate when the distance between the longitudinally extending probe in the medical instrument is less than desirable and when this occurs, a notification is created at 614. In some implementations, this preset distance threshold may be fixed within the control system 20. The distance threshold may be established based on any of a number of factors including, for example, the health care providers skill or experience level, the type of instrument used, the type of surgery performed, user preference, the sensitivity of the tubular body structure, the average diameter of the tubular body structure containing the longitudinally extending probe, or other factors. In some implementations, the preset distance threshold may form a boundary which completely radially encompasses the tubular body structure containing the longitudinally extending probe. Some implementations permit a health care provider or other healthcare provider to adjust the setting prior to or during performing the surgical procedure.

In some implementations, the notification module 206 of the control system 20 may monitor the distance between the longitudinally extending probe and the medical instrument and compare the distance to the distance threshold. If the distance between the longitudinally extending probe and the medical instrument is not below the threshold, then the method returns to 606 and the system continues to determine the position of the longitudinally extending probe and the medical instrument. If the distance between the longitudinally extending probe and the medical instrument is below the threshold, then the control system may generate a notification to alert the health care provider at 614. This notification may include creating a visual, audible, or tactile alert to let the health care provider know that the surgical instrument is within a safety zone dictated by the threshold. In some implementations, generating a notification includes presenting information on the display of the operator control and display system. This may include flashing a dimension in the corner of the screen or may include other dynamic visual indicators to alert the operator to the elevated risk. In some implementations, the control system may respond by preventing or discouraging but allowing further movement of the medical instrument toward the longitudinally extending probe. This may mechanically prevent the health care provider from inadvertently engaging the tubular body structure with the medical instrument.

Some examples of processors may include non-transient, tangible, machine readable media that include executable code that when run by one or more processors may cause the one or more processors to perform the processes of method 600. Some common forms of machine readable media that may include the processes of method 600 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A system for identifying a location of a lumen of a tubular body structure in a patient's body, comprising:
   a flexible, longitudinally extending probe configured to be inserted through the lumen in the tubular body structure in the patient, the probe comprising a longitudinally extending detectable portion;
   a teleoperated medical system comprising a surgical tool arranged to interact with the patient's body; and
   a control system comprising:
      an antenna array arranged to receive signals from the longitudinally extending detectable portion of the probe, and
      a processing system arranged to establish a radially-shaped boundary, wherein the radially-shaped boundary completely radially encompasses the tubular body structure in the patient and includes a diameter larger than a diameter of the tubular body structure in the patient providing a safety zone when the longitudinally extending detectable portion of the probe is disposed in the tubular body structure, the processing system configured to process the received signals and identify a longitudinally extending position of the longitudinally extending detectable portion of the probe in a three-dimensional reference frame, the processing system configured to identify a position of the surgical tool by calculating the position of the surgical tool within the three-dimensional reference frame taking into account an orientation of components of the teleoperated medical system;

wherein the processing system is arranged to compare the identified position of the longitudinally extending detectable portion of the probe to the position of the surgical tool in the patient's body to determine a distance between the identified position of the longitudinally extending detectable portion of the probe and the position of the surgical tool; and wherein the processing system is arranged to activate a notification when the surgical tool is within the radially-shaped boundary of the longitudinally extending detectable portion of the probe in the tubular body structure.

2. The system of claim 1, wherein the control system comprises an RF or microwave detection system that receives signals from the longitudinally extending detectable portion.

3. The system of claim 1, wherein the surgical tool is one of an instrument tip, a cannula, or an endoscope.

4. The system of claim 1, comprising a display viewable by a health care provider, the processing system being arranged to overlay an image of the location of the longitudinally extending detectable portion of the probe over viewable images on the display.

5. The system of claim 1, wherein the longitudinally extending detectable portion comprises a plurality of spaced detectable segments.

6. The system of claim 1, wherein the antenna is a pad with a plurality of spaced antennas, the pad being arranged to be disposed adjacent to and external of the patient's body.

7. The system of claim 1, wherein the antenna comprises an array of RF transmitters and RF receivers.

8. The system of claim 1, wherein the probe comprises an array of microwave receivers.

9. The system of claim 1, wherein the notification is one of a flashing alert on a display, a change in color, a textual message display, an audible alarm, or a tactile alert.

10. The system of claim 1, wherein the control system comprises a pad disposable upon an operating table under the patient, the pad comprising the antenna array arranged to receive the signals from the longitudinally extending detectable portion of the probe, the antenna array comprising all antennas of the control system.

11. The system of claim 1, wherein the antenna array is disposed in a mat sized to fit on a bed underneath the patient.

12. The system of claim 11, wherein the mat comprises antennas aligned in rows and columns.

13. A system for detecting a location of a lumen of a tubular body structure in a patient's body relative to a location of a surgical tool, comprising:
a flexible, longitudinally extending probe configured to be inserted through the lumen in the tubular body structure of the patient, the longitudinally extending probe having a longitudinally extending detectable portion along a longitudinal length;
a teleoperated medical system comprising a surgical tool arranged to interact with the patient's body to perform a surgical task on the patient; and
a control system arranged to establish a radially-shaped boundary, wherein the radially-shaped boundary completely radially encompasses the tubular body structure in the patient and includes a diameter larger than a diameter of the tubular body structure in the patient providing a safety zone when the longitudinally extending detectable portion of the probe is disposed in the tubular body structure, the control system configured to a) detect a longitudinally extending position of the longitudinally extending detectable portion, b) calculate a position of the surgical tool within a three-dimensional reference frame taking into account an orientation of components of the teleoperated medical system, and c) compare the detected longitudinally extending position of the longitudinally extending detectable portion to the position of the surgical tool in the patient's body to inhibit undesired interference between the tubular body structure containing the longitudinally extending detectable portion and the surgical tool, the control system configured to activate a notification when the surgical tool is within the radially-shaped boundary of the longitudinally extending detectable portion of the probe in the tubular body structure.

14. The system of claim 13, wherein the control system comprises an antenna array arranged to receive signals from the longitudinally extending detectable portion.

15. The system of claim 13, wherein the surgical tool is one of an instrument tip, a cannula, and an endoscope.

16. The system of claim 13, comprising a display viewable by a health care provider and a processing system being arranged to overlay an image of the longitudinally extending detectable portion over viewable images on the display.

17. The system of claim 13, wherein the notification is one of a flashing alert on a display, a change in color, a textual message display, an audible alarm, or a tactile alert.

18. The system of claim 13, wherein the control system comprises a pad disposable upon an operating table under the patient, the pad comprising an antenna array arranged to receive signals from the longitudinally extending detectable portion of the probe, the antenna array comprising all antennas of the control system.

19. A method comprising:
inserting a flexible, longitudinally extending probe through a lumen in a tubular body structure in a patient, the longitudinally extending probe having a longitudinally extending detectable portion;
inserting a surgical tool in a patient with a teleoperated medical system;
generating a radially-shaped boundary, wherein the radially-shaped boundary completely radially encompasses the tubular body structure in the patient and includes a diameter larger than a diameter of the tubular body structure in the patient providing a safety zone when the longitudinally extending detectable portion of the probe is disposed in the tubular body structure;
calculating a position of the surgical tool within a three-dimensional reference frame taking into account an orientation of components of the teleoperated medical system;
detecting a longitudinally extending position of the longitudinally extending detectable portion of the extending probe in the three-dimensional reference frame with an antenna arranged to receive signals from the longitudinally extending detectable portion;
comparing the detected longitudinally extending position of the longitudinally extending probe to the position of the surgical tool in the patient's body to determine whether the detected position of the longitudinally extending position of the longitudinally extending probe is within the radially-shaped boundary; and
activating a notification when the surgical tool is within the radially-shaped boundary of the longitudinally extending detectable portion of the probe in the tubular body structure.

20. The method of claim 19, wherein activating the notification comprises activating one of a flashing alert on a display, a change in color, a textual message display, an audible alarm, or a tactile alert.

21. The method of claim 19, wherein the antenna is formed in a pad disposable upon an operating table under the patient, the antenna comprising an antenna array arranged to receive the signals from the longitudinally extending detectable portion of the probe, the pad comprising all antennas that receive the signals from the longitudinally extending detectable portion.

22. A system for identifying a shape of a plastic encased braided metallic structure inserted into an anatomical structure in a body, comprising:
   a plastic encased braided metallic structure inserted into the body through a natural orifice, comprising a longitudinally extending detectable portion;
   a teleoperated medical system comprising a surgical tool arranged to interact with the body; and
   a control system comprising:
      an antenna arranged to bounce signals off the longitudinally extending detectable portion, and
      a processing system configured to process received signals and identify a braided metallic structure position of the longitudinally extending detectable portion of the plastic encased braided metallic structure in a three-dimensional reference frame;
      the processing system arranged to establish a radially-shaped boundary, wherein the radially-shaped boundary completely radially encompasses the anatomical structure in the body and includes a diameter larger than a diameter of the anatomical structure of the body providing a safety zone when the longitudinally extending detectable portion of the plastic encased braided metallic structure is disposed in the anatomical structure, the processing system configured to identify a position of a surgical tool by calculating the position of the surgical tool within the three-dimensional reference frame taking into account an orientation of components of the teleoperated medical system; and
      the processing system configured to compare the identified position of the braided metallic structure position to the position of the surgical tool to determine a distance between the identified position of the braided metallic structure position and the position of the surgical tool; and
      wherein the processing system is arranged to activate a notification when the surgical tool is within the radially-shaped boundary of the braided metallic structure position.

23. The system of claim 22, wherein the notification is one of a flashing alert on a display, a change in color, a textual message display, an audible alarm, or a tactile alert.

24. The system of claim 22, wherein the antenna is disposed in a pad disposable upon an operating table under the body, the pad comprising all antennas of the control system.

* * * * *

UNITED STATES PATENT AND TRADEMARK OFFICE
CERTIFICATE OF CORRECTION

PATENT NO. : 12,207,885 B2  
APPLICATION NO. : 16/140709  
DATED : January 28, 2025  
INVENTOR(S) : Ian E. McDowall, Marc Levesque and Theodore W. Rogers Page 1 of 1

It is certified that error appears in the above-identified patent and that said Letters Patent is hereby corrected as shown below:

In the Claims

Column 18, Line 52, Claim 19, add -- longitudinally -- after "of the"

Signed and Sealed this  
Eighth Day of April, 2025

Coke Morgan Stewart  
*Acting Director of the United States Patent and Trademark Office*